US006808924B1

(12) United States Patent
Lanari et al.

(10) Patent No.: US 6,808,924 B1
(45) Date of Patent: Oct. 26, 2004

(54) MOUSE MAMMARY TUMOR LINES EXPRESSING ESTROGEN AND PROGESTERONE RECEPTORS

(76) Inventors: Claudia Lanari, Combate de San Lorenzo 266, Buenos Aires 1617 (AR); Alfredo Molinolo, Cabrera 5809, Buenos Aires 1414 (AR); Isabel Luthy, Luis Saenz Pena 151, 8 "C" , Buenos Aires 1110 (AR)

( * ) Notice: Subject to any disclaimer, the term of this patent is extended or adjusted under 35 U.S.C. 154(b) by 0 days.

(21) Appl. No.: 09/613,707

(22) Filed: Jul. 11, 2000

(51) Int. Cl.[7] .................................................. C12N 5/06

(52) U.S. Cl. ...................................... 435/354; 435/325

(58) Field of Search .............................. 435/7.21, 70.3, 435/325, 354

(56) References Cited

U.S. PATENT DOCUMENTS

| 3,962,449 A | 6/1976 | Binnig et al. |
| 4,459,301 A | 7/1984 | Binnig et al. |
| 4,550,112 A | 10/1985 | Schoen et al. |
| 4,556,662 A | 12/1985 | Binnig et al. |
| 4,912,113 A | 3/1990 | Schoen et al. |
| 4,959,373 A | 9/1990 | Lubisch et al. |
| 5,468,858 A | 11/1995 | Berlin et al. |
| 5,576,327 A | 11/1996 | Schoen et al. |
| 5,786,481 A | 7/1998 | Berlin et al. |

FOREIGN PATENT DOCUMENTS

| EP | 0 306 871 A2 | 3/1989 |
| EP | 0 308 843 | 3/1989 |
| EP | 0 308 848 A | 3/1989 |
| EP | 0 665 228 A1 | 8/1995 |
| WO | 91/07405 | 5/1991 |
| WO | 97/17961 | 5/1997 |
| WO | 99/31100 | 6/1999 |
| WO | 00/61569 | 10/2000 |
| WO | 00/71529 | 11/2000 |

OTHER PUBLICATIONS

Darnell et al (1990, Molecular Cell Biology, p. 710 and 711 only).*
Dran, et al., 1995, Breast Cancer Reseach and Treatment, 35:173–86.*
Villa et al, "3,8–Diazabicyclo . . . ," Eur. J. Med. Chem., vol. 36, pp. 495–506 (2001).
Reis, Lynn. "Top 5 Cancers for Females & Males in the U.S." Natl Cancer Inst. 87: 867 (1995).
Jensen, O. et al., "Cancer in the European Community and its Member States" Eur. J. Cancer 26: 1167–1256 (1990).
Boring, Catherine et al., "Cancer Statistics" Cancer J. Clin. 43: 7–26 (1993).
Miller, Barry A. et al., "The Increasing incidence of breast cancer since 1982: relevance of early detection" Cancer Causes Control 2:67–74 (1991).
Levi, F., "Cancer Incidence in Five Continents, vol. VI" Eur J Cancer 29:2315–2319 (1993).
Corry, J.F. and Lonning, PE., Pharmacol. Econom 5: 198–212 (1994).
Welsch, C.W. and Nagasawa, H., "Prolactin and Murine Mammary Tumorigenesis: A Review" Cancer Res 37:951–963 (1977).
Sluyser, M. and Van Nie, R., "Estrogen Receptor Content and Hormone–responsive Growth of Mouse Mammary Tumors" Cancer Res 34:3253–3257 (1974).
Michalides, R. et al., "Mouse Mammary Tumor Virus Expression and Mammary Tumor Development" Current Topics in Microbiology and Immunology, vol. 106, pp 57–78 (1983).
Pogo, BG. et al., 1997 Medicina (Buenos Aires)57 Suppl 2:75–80.
Guillino, P. et al., "n–Nitrosomethylurea as Mammary Gland Carcinogen in Rats" J Natl Cancer Inst. 54:401–404 (1975).
Russo, J. et al., Differentiation of the mammary gland and susceptibility to carcinogenesis Breast Cancer Res and Treat 2:5–73 (1982).
IP, C., "Mammary Tumorigenesis and Chemoprevention Studies in Carcinogen–Treated Rats" J. Mammary Gland Biol Neopl 1: 37–47 (1996).
Soule, H.D. et al., "A Human Cell Line From a Pleural Effusion Derived from a Breast Carcinoma" J Natl Cancer Inst 51:1409–1416(1973).
Engel L, W. et al., "Establishment and Characterization of Three New Continuous Cell Lines Derived from Human Breat Carcinomas" Cancer Res. 38: 3352–3364 (1978).
Keydar I. et al., Cancer 51:659–670 (1979).
Whitehead RH. et al., "A New Human Breat Carcinoma Cell Line (PMC42) with Stem Cell Characteristics. III. Hormone Receptor Status and Responsiveness" J Natl Canc Inst. 73:643–648 (1984).
Yamane, M. et al., "Establishment and Characterization of New Cell Line (YMB–1) Derived from Human Breast Carcinoma" Hiroshima J Med Sci 33:715–720 (1984).
Vandewalle B. et al., "Establishment and characterization of a new cell line (VHB–1) derived from a primary breast carcinoma" J Cancer Res. Clin. Oncol. 113:550–558 (1987).
Siwek B. et al., "Establishment and Characterization of Three New Breast–Cancer Cell Lines" Int J Cancer 76:677–683 (1998).

(List continued on next page.)

*Primary Examiner*—Larry R. Helms
*Assistant Examiner*—Misook Yu
(74) *Attorney, Agent, or Firm*—Fulbright & Jaworski, LLP

(57) ABSTRACT

The invention relates to the generation of mouse mammary adenocarcinoma cell lines which express estrogen and progesterone receptors as a tool to study the effect of hormones, pharmacological compounds and environmental agents. The invention also relates methods in vitro and in vivo for testing hormones or another related molecules by cell proliferation or tumor proliferation.

2 Claims, 10 Drawing Sheets

OTHER PUBLICATIONS

Mobus, V.J. et al., "Differential Characteristics of Two New Tumorigenic Cell Lines of Human Breast Carcinoma Origin" Int J Cancer 77:415–423 (1998).

Clarke R., "Human Breast Cancer cell line xenografts as models of breast cancer—The immunobiologies of recipient mice . . . ". Breast Cancer Res and Treat 39: 69–86 (1996).

Amundadottir, L.T. et al. "Transgenic mouse models of breast cancer" Breast Cancer Res and Treat 39:119–135 (1996).

Kiss, R. et al. "Influence of Pituitary Grafts or Prolactin Administations . . ." Cancer Res 49:2945–51(1989).

Sacco, M.G. et al "Establishment and characterization of a new mammary adenocarcinoma cell line . . . " Breast Cancer Res and Treat 47:171–180 (1998).

Lanari, C. et al, "Induction of Mammary Adenocarcinomas by Medroxyprogesterone Acetate in Balb/c Female Mice" Cancer Letters 33: 215–223. (1986).

Molinolo, A.A. et al "Mouse Mammary Tumors Induced by Medroxyprogesterone Acetate: Immunohistochemistry and Hormonal Receptors" JNCI 79:1341–1350 (1987).

Dran, G. et al. "Effect of medroxyprogesterone acetate (MPA) and serum factors on cell proliferation in primary cultures of an MPA–induced mammary adenocarcinoma" Breast Canc Res and Treat 35:173–86 (1995).

Paroczai et al, "Investigations to Characterize a New . . . ," Pharmacological Research, vol. 24, No. 2, pp. 149–162 (1991).

Chen et al, "High–Performance Liquid . . .," Analytical Sciences, vol. 9, pp. 429–451 (1993).

Garrison et al, "Novel 3,7–Diheterabicyclo[3.3.1] nonanes. . . ," J. Med. Chem., vol. 39, pp. 2559–2570 (1996).

Wang et al, "Class III Antiarrhythmic Drug Action . . . ," Circulation, vol. 90, No. 4, pp. 2032–2040 (1994).

* cited by examiner

MOUSE MAMMARY TUMOR LINES EXPRESSING ESTROGEN AND PROGESTERONE RECEPTORS

FIELD OF THE INVENTION

The present invention relates to mouse mammary adenocarcinoma cell lines expressing estrogen and progesterone receptors as a tool to study the effect of hormones, pharmacological compounds, and environmental agents. The present invention also relates to methods in vitro and in vivo for testing hormones or other related molecules by cell proliferation or tumor proliferation.

BACKGROUND OF THE INVENTION

Epithelial breast malignant neoplasms of the mammary gland is one of the most common form of cancer among women in North America, South America, Europe, and Australia, and they account for 15–18% of the deaths in this population (Lynn and Reiss, 1995 J. Natl Cancer Inst. 87: 867; Moller Jensen et al., 1990 Eur. J. Cancer 26: 1167–1256; Boring et al., 1993 Cancer J. Clin. 43: 7–26). Despite the development of different therapeutic approaches, the mortality has continued to rise over the past thirty years: the incidence of breast cancer is increasing by about 1% per year in almost all populations in both industrialized and developing countries (Miller et al., 1991 Cancer Causes Control 2:67–74; Levi F., 1993 Eur J Cancer 29:2315–2319), and it is estimated that the disease will affect 5 million women in the next decade (Corry J F. and Lonning P E., 1994 Pharmacol. Econom 5: 198–212). Obviously, within the aging female population, prevention and treatment of breast cancer will continue to represent a major challenge.

The etiology of breast cancer remains largely unknown, and the dilemma of mammary tumor development and the related mechanisms have been studied with different experimental approaches. The virus-induced mouse mammary tumor (MMTV) model had different drawbacks; most of the tumors induced by MMTV are not hormone responsive or are pregnancy-responsive (Welsch C W and Nagasawa H., 1977 Cancer Res 37:951–963; Sluyser M. and Van Nie R., 1974 Cancer Res 34:3253–3257), and no definite involvement was demonstrated for a virus in the etiology of breast tumors in humans (Michalides R. et al., Current Topics in Microbiology and Immunology, Vol. 106, Eds: P K Vogt y H Koprowski, Springer Verlag, Berlin, pp57–78; Pogo B G. et al., 1997 Medicina (Buenos Aires)57 Suppl 2:75–80). The chemical carcinogen models allowed the dissection of initiators and promoters; the tumors originated in both the MNU and the DMBA rat models were hormone-responsive, and they expressed estrogen receptors (ER) (Gullino P. et al., 1975 J Natl Cancer Inst. 54:401–404; Russo I H. et al., 1982 Breast Cancer Res and Treat 2:5–73). They did not, however, give rise to metastasis, and they harbored point mutations in certain oncogenes not found in the human disease that are probably related to the chemical carcinogen (Ip C., 1996 J. Mammary Gland Biol Neopl 1: 37–47).

Other approaches involve the establishment of human cell lines. The most widely used human breast cancer cell lines are the MCF-7 (Soule H D. et al., 1973 J Natl Cancer Inst 51:1409–1416); the T-47-D (Engel L W. et al., 1978 Cancer Res. 38: 3352–3364); and the ZR-75–31 (Keydar I. et al., 1979 Cancer 51: 659–670). These lines express ER and progesterone receptors (PR) and are hormone responsive. In the last years, other cell lines have been established: PMC42 (Whitehead R H. et al., 1984 J National Cancer Institute 73:643–648); YMB-1 (Yamane M. et al., 1984 Hiroshima J Med Sci 33:715–720); VHB (Vandewalle B. et al., 1987 J Cancer Res Clin Oncol 113:550–558); IBEP-1, IBEP-2 and IBEP-3 (Siwek B. et al., 1998 Int J Cancer 76:677–683); BrCa-MZ-01 and BrCa-MZ-02 (Mobus V J. et al., 1998 Int J Cancer 77:415–423). A part of our knowledge on hormone regulation of cell growth has been deduced from experiments performed using these lines. Approximately twenty cell lines, which express hormone receptors, are available and have been used in other types of experiments. It is well-known that valuable initial information can be gathered from in vitro studies. However, cancer occurs in the context of a complex interaction with its surrounding environment, e.g., neighboring tissues, the immune system, hormones, and environmental factors. Thus, there is a trend to study either xenografts in immune-suppressed mice (Clarke R. 1996 Breast Cancer Res and Treat 39: 69–86) or transgenic or knock-out mice (Amundadottir L T. Et al. 1996 Breast Cancer Res and Treat 39:119–135). A problem with most cell lines is that they are not metastatic unless they are transfected with different growth factors, and also the high costs of immuno-suppressed mice. In mice there are few models which have been used to study hormone regulation in tumor growth, among than them MXT model and the GR mice. The former is a mammary tumor which is maintained by syngeneic transplantation and expresses high levels of ER and PR (Kiss R. et al. 1989 Cancer Res 49:2945–2951). The latter is a E) strain of mice which develops pregnancy-dependent tumors (Sluyser M. and Van Nie R. 1974 Cancer Res 34:3253–3257). No cell lines have yet been developed from mouse tumors which maintain steroid receptor expression except for a tumor induced in c-erbB2 transgenic mice (Sacco M G. Et al 1998 Breast Cancer Res and Treat 47:171–180).

The inventors have developed an experimental model in which ductal metastatic, progestin-dependent (PD) mammary adenocarcinomas are induced by the continuous administration of MPA to BALB/c female mice; these tumors express high levels of ER and PR (Lanari C. et al 1986 Cancer Letters 33: 215–223., Molinolo A A. et al 1987 JNCI 79:1341–1350), and are maintained through syngeneic serial passages in MPA-treated mice. By transplantation into untreated mice, the inventors have been able to generate progestin-independent (PI) tumor lines that retain the expression of ER and PR. In in vitro studies, using primary and secondary cultures of one of these PD tumor lines (C4-HD), the inventors were able to demonstrate that MPA stimulates directly cell proliferation and that antiprogestins inhibit cell growth even at very low concentrations (Dran G. et. al. 1995 Breast Cancer Res and Treat 35: 173–186).

Earlier in the characterization of the experimental model, with the aim of further dissecting certain aspects of the hormonal response, the inventors developed a technique to obtain purified epithelial or fibroblastic primary cultures from these tumors (Dran G. et al. 1995 Breast Cancer Res and Treat 35:173–186). Although primary cultures are an excellent tool to study the direct effect of hormones on cell proliferation, the approach is time consuming, e.g., many different controls need to be performed in parallel, to be able to bypass the inherent heterogeneity of every primary culture, and standardize the findings.

To overcome these shortcomings, in the setting of the characterization of the different isoforms of the PR expressed by the tumors, the inventors decided to attempt to develop continuous cell lines in which different parameters regarding hormone dependence could be studied. The inventors were able to develop four cell lines derived from one PD tumor and one from a PI tumor. This is the first description of mouse mammary adenocarcinoma cell lines obtained in non transgenic animals which express ER and PR.

The inventors provided a cell line panel for screening hormones and related molecules.

SUMMARY OF THE INVENTION

In accordance with the present invention, cell lines and methods for screening hormones are provided.

The present invention relates two mouse mammary adenocarcinoma cell lines MC4-L1 and MC4-L3, which are derived from a murine progestin-dependent CC4-HD tumor, wherein the cell lines express ER and PR and are deposited in the American Type Culture Collection (ATCC) as Accession number PTA-889 and PTA-891.

The present invention also relates a cell line, MC4-L2, obtained by subcloning of cell line MC4-L1 deposited with the ATCC as Accession number PTA-892

The present invention also relates to a mouse mammary adenocarcinoma cell line MC7-L1 which is derived from the murine progestin-independent C7-H1 tumor, wherein the cell line expresses ER and PR and have been deposited on Oct. 28, 1999 with American Type Culture Collection (ATCC), 1081 University Blvd, Manassas, Va. 20110-2209 ATCC Accession number PTA-890.

A further object of the invention is to provide a cell culture system that will facilitate the screening and identification of agents that may be clinically relevant in the treatment of cancer. This cell line system will also find utility in the identification of compounds that have therapeutic value for other illnesses, e.g., endocrine disorders and other hormone-replacement therapies. A cell line system is provided for identifying, detecting or quantitating substances suspected of binding ER and PR.

The cell culture system of the present invention will be useful as a research tool rand will facilitate the elucidation of the mechanistic action of novel substances that bind ER and PR.

The present invention provides an in vitro method for testing the activity of hormones, anti-hormones, pharmacological compounds and environmental agents on cell lines. This method comprises exposing the cell lines MC4-L1, MC4-L3, MC4-L2 and MC7-L1 to hormones, anti-hormones, pharmacological compounds and environmental agents and then evaluating the cell proliferation by using any cellular proliferation method known by those skilled in the art. This includes 3H-thymidine uptake, MTT assay, MTS assay, and the like thereof.

The present invention also provides an in vivo method for testing the activity of hormone, anti-hormone, pharmacological compounds and environmental agents by inoculating cell lines MC4-L1, MC4-L3, MC4-L2 and MC7-L1 in syngeneic mice, allowing the tumors to grow to about 50 mm$^2$ and applying a dose of the compounds to be evaluated daily and then analyzing the tumor size (tumor growth), tumor regression, number of metastases, prolongation of survival or any other parameter known to the experts in order to determine the activity of molecules tested on the tumor.

The cell lines and methods of the present invention provide a system for the analysis of hormones and related molecules without the need for primary tissue cultures.

It is an object of this invention to provide a kit that is highly useful for testing the activity of hormones, anti-hormones, pharmacological compounds and environmental agents. The kit comprises an aliquot of cell lines MC4-L1, MC4-L3, MC4-L2 and MC7-L1 and a method to evaluate cellular proliferation.

As described herein, the term "agents that may be clinically relevant in the treatment of cancer" comprises compounds or molecules that elicit a proliferative response through binding the PR or ER, such as, but not limited to, medroxyprogesterone acetate or R5020, diethylstylbestrol.

As described herein, "anti-hormone" comprises molecules or compounds acting by inhibiting the proliferative activity of the above mentioned compounds, for example, but not limited to, mifepristone, ZK or tamoxifen, and raloxifene.

As described herein, "cell line" comprises cells that initially derived from a tumor. Such cells have indefinite growth in culture; unlike primary cultures, which can be maintained only for a finite period of time. Moreover, such cells preferably can form tumors after they are injected into syngeneic animals.

According to the invention "Cancer" includes cancers, in particular breast cancer.

As described herein, "cellular proliferation" means an increasing in the cell number analyzed by any method known in the art, for example 3H-thymidine uptake, MET assay, MTS assay, relative to an untreated control.

As described herein, "tumor growth" includes an increase in tumor size and "tumor regression" includes a reduction in tumor mass.

As described herein, "tumor line" includes tumors that express high levels of ER and PR, and are maintained through syngeneic serial passages in MPA-treated mice or into untreated mice.

As described herein, RU is mifepristone or RU38486; ZK is onapristone or ZK 98299.

DETAILED DESCRIPTION OF THE INVENTION

Figure 1:
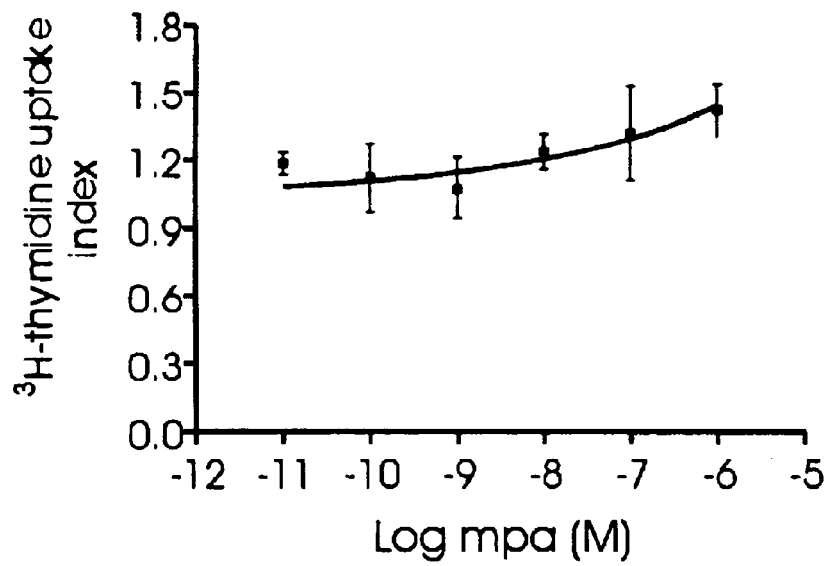
FIG. 1 illustrates the effect of MPA on MC4-L1 cell line proliferation. 3H-Thymidine uptake index represents the ratio between cpm of experimental group vs control. The mean value of 3–15 experiments is shown.

All references cited herein are hereby incorporated by reference. In case of inconsistencies, the present disclosure governs.

The invention relates to the generation of mouse mammary adenocarcinoma cell lines which express ER and PR as a tool to study the effect of hormones, pharmacological compounds and environmental agents. The present invention also relates methods in vitro and in vivo for testing hormones or another related molecules by cell proliferation or tumor proliferation.

Tissue used to establish the cell lines was obtained from a progesterone-dependent ductal MPA-induced adenocarcinomas (CC4-HD): at passage 60 maintained by syngeneic transplantation in MPA-treated mice and a PI tumor (C7-HI) also obtained from an MPA-treated mouse which was maintained by syngeneic transplantation in untreated female mice (Lanari et al, 1986; Molinolo et al, 1987). The main difference between both tumor lines can be observed in Table 1. CC4-HD originated from a primary culture of C4-HD transplanted sc in an MPA-treated mouse.

TABLE 1

Parental tumor line features CC4-HD and C7-HI

| Feature | CC4-HD | C7-HI |
|---|---|---|
| Origin | Originated in 1985 in BALB/c mice treated with depot MPA 40 mg every three months (JNCI 1986; 77:157–164). Group C, cage 4 for CC4-HD and cage 7 for C7-HI. The first C stands for the primary culture re-inoculated. The HD or HI ending was added in accordance to the ability to grow in progestin-treated or untreated animals. | |
| Histology | Ductal mammary carcinomas | |
| Hormone dependence | Progestin-dependent (PD) | Progestin-independent (PI) |
| Metastasis | Lung after 4–5 months | Auxillary homolateral lymph nodes and lungs before two months. |
| ER (fmol/mg prot; X ± SD) | 63 ± 20 (n = 6) | 34 ± 8 (n = 6) |
| PR (mol/mg prot; X ± SD) | 171 ± 54 (n = 6) | 160 ± 48 (n = 6) |
| Glucocorticoid receptors | | Negative |
| Androgen receptors | | Negative |
| EGF receptors | | Negative |
| c-erbB2 amplification | Yes | No |

The primary culture was an epithelial enriched culture. The medium is DMEM/F12 without Phenol Red. Ten days after seeding, cells became vacuolated and some of them started to detach; fibroblasts which were very scanty at the beginning increased in proportion. During the next 2–3 months, the presence of giant multinucleated cells was the most conspicuous feature.

Some wells were subcultured from big wells to smaller ones. The cells that did not attach for the first hour were transferred to another well, and the cells which did not attach in this second well for two hours were transferred to another well. This was performed in order to remove fibroblasts. Curiously, cell lines arose from epithelial clusters present in these fast-attaching cell populations. Five or six subcultures were performed during 3–4 months, and in each subculture less cells were harvested. From 2 different primary cultures of the CC4HD tumor lines, 3 cell lines were developed, one of these, MC4-L2, is a subline derived from MC4-L1. A small group of cells from passage 7 of MC4-L1 remained attached after trypsinization. With time, these cells started to grow with a completely different pattern than that of the parental cells.

A similar phenomenon occurred with MC7-L1. Colonies of giant cells can also been seen, but in this case, there were a different kind of cells intermingled with giant "fibroblast-like" cells and the cell line arose from wells where the general morphological aspect was of scanty epithelial cells intermingled with a mass of fibroblast like cells.

In summary, 3 lines arose from CC4-HD and one from C7-HI.

Several tests were used to characterize the resultant cell lines. The origin of the four cell lines was evaluated by immunocytochemistry of intermediate filaments (cytokeratin); and the expression of hormone receptors by immunocytochemistry and biochemical assays.

The medium and medium components are readily available and can be obtained, for instance, from commercial suppliers. Such commercial suppliers include, but are not limited to, Gibco BRL (Gaitherberg, Md.), Sigma Bioscience (St. Louis, Mo.), Gen S. A. (Buenos Aires) and other suppliers manufacturating similar products.

The tumor cell lines can be used, for instance, for monitoring hormones and related molecules either in vitro or in vivo.

Morphological aspects of the cell lines

In Vitro

MC4-L1 was the first line obtained from a CC4HD parental tumor line that presents a PD pattern of tumor growth. Cells vary in size and have the typical polygonal epithelial shape. Giant cells were always present even after 70 subcultures. MC4-L2 originated from one of the wells of the 8th subculture passage of MC4-L1. After trypsinization, the few that remained undetached were left with medium as a back up in case of contamination. After a month without any medium change, a morphologically different cell population arose. These spindle-shaped cells, now named MC4-L2, grew as isolated cells, but eventually coalesced in cumuli when the culture was overgrown. MC4-L3 arose from a different primary culture performed two weeks after the one that originated from the two previous lines. Although its morphology resembles that of MC4-L1, the cells were more homogeneous in size.

MC7-L1 arose from a different in vivo tumor line, with a PI pattern of growth, as explained previously. These cells were similar to MC4-L2 cells, with spindle-shape morphology, even more elongated than MC4-L2, and they also grew as single cells.

Tumors

When these cells were inoculated into BALB/c female mice, they gave rise to metastatic carcinomas. MC4-L1 originated ductal infiltrating carcinomas with tubular and cribiform differentiation. Polygonal or flat proliferating cells showed a pale nucleus with lax chromatin and one or two nucleoli. Mitotic and apoptotic figures were frequently detected. Necrosis was frequently found in the center of tumor masses. The stroma was scanty, dense and well vascularized. Lung metastasis were detected three months after tumor inoculum, invading and destroying the normal lung tissue.

A completely different picture was observed with MC4-L2. These cells give rise to sarcomatoid tumors disclosing local invasion and lung and lymph node metastases. Fusiform cells infiltrating muscular tissue were often found. Although they were well vascularized, stroma was scanty and groups of mastocyte-like cells are frequently found. Atypical proliferating cells showed giant nuclei or were multinucleated. Focus of epithelial like cells were also seen. Cytokeratin staining confirmed their epithelial origin.

MC4-L3 showed no signs of glandular differentiation. Proliferating cells disclosed ovoid nuclei with one or no nucleoli and pale cytoplasms of variable sizes. The stroma was abundant, lax, and fibroblastic. Areas of necrosis and thrombosis were also observed.

MC7-L1 growing in vivo, resembled an undifferentiated carcinoma, with polygonal cells showing dense and eosinophylic cytoplasms, arranged in solid masses without structural differentiation. Multinucleated cells showing atypical ovoid or hyperchromatic nuclei were observed. A high mitotic index (greater than 20/field 40x) was registered. These tumors also infiltrated neighbor tissues and gave rise to distant metastases. Lung metastases showed a more epitheloid appearance than the primary tumor.

Cytokeratin Staining

All cell lines, including MC4-L2 and MC7-L1 that showed a fibroblastic-like morphology when growing in vitro, showed positive staining when reacted with anticytokeratin antibodies.

The epithelial morphology was also assessed in the tumors. The four cell lines gave rise to tumors which were positive to cytokeratins. Again, it can be noticed that MC4-L2 gave rise to sarcomatoid tumors which were positive to cytokeratins, confirming their epithelial origin.

The tumor cell lines of the present invention demonstrated cytokeratin staining upon histochemical staining using an antibody directed against cytokeratin. Accordingly, the present invention provides preferred cell lines including MC4-L1, MC4-L2, MC4-L3 and MC7-L1.

Estrogen and progesterone receptor expression

ER and PR were detected by immunocytochemical and biochemical methods. All cell lines, showed intense nuclear staining confirmed using biochemical methods by single saturation points.

Similar results were obtained when the tumors were studied. Both primary tumors and their metastasis show intense nuclear staining for both ER and PR.

c-erbB2 expression

MC4-L1, MC4-L2 and MC4-L3 showed intense c-erbB2 staining. These results were in agreement with previous results showing showing c-erbB2 amplification in the parental C4-HD tumor line (Balaña, ME et al 1999 Oncogene 18: 6370–6379).

Detachment

MC4-L1 and MC4-L3 cells showed a strong adhesion to plastic, since it took more Man 10 minutes to detach after trypsin treatment. In contrast, MC4-L2 and MC7-L1 easily detached only a few seconds after trypsin treatment or even without enzymatic solution, just by shaking.

In Vitro hormone response

In one embodiment of the invention, the response of cells to a progestin: MPA, an estrogen: $E_2$, 2 antiprogestins: RU, ZK, an antiestrogen: ICI and TGFβ1 was studied using the currently protocol. These methods are well known to those of ordinary skill in the art.

MC4-L1

Figure 2:
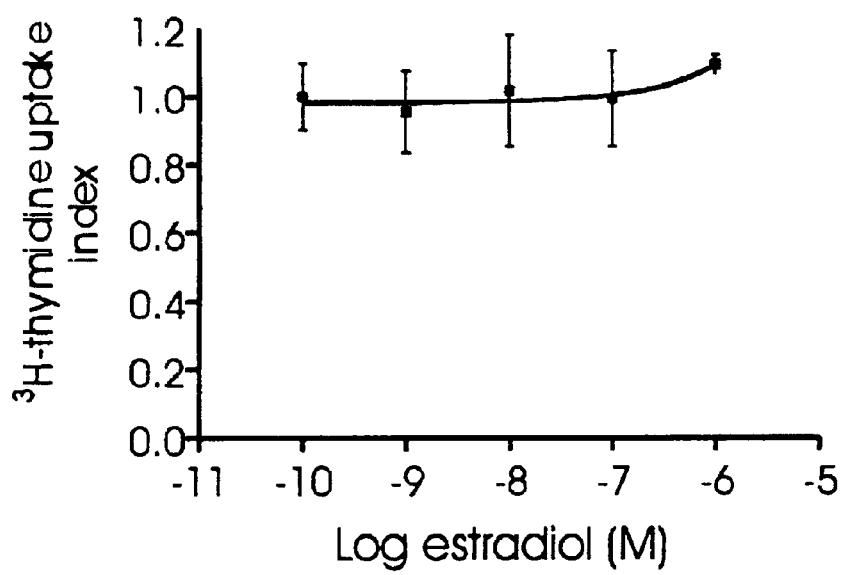
FIG. 2 illustrates the effect of estradiol (E$_2$) on MC4-L1 cell line proliferation. 3H-Thymidine uptake index represents the ratio between cpm of experimental group vs control. The mean value of 3–15 experiments is shown.
Figure 3:
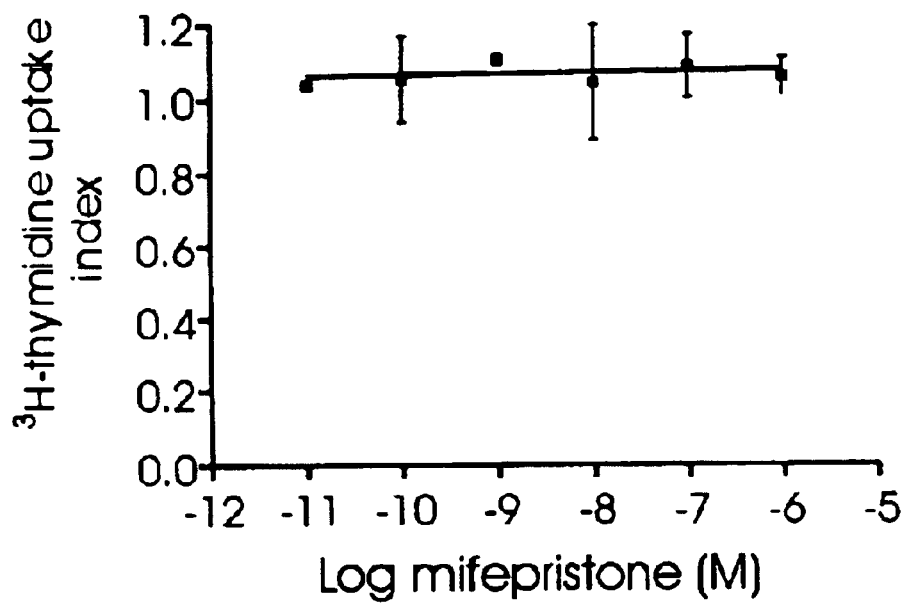
FIG. 3 illustrates the effect of miefepristone on MC4-L1 cell line proliferation. 3H-Thymidine uptake index represents the ratio between cpm of experimental group vs control. The mean value of 3–15 experiments is shown.
Figure 4:
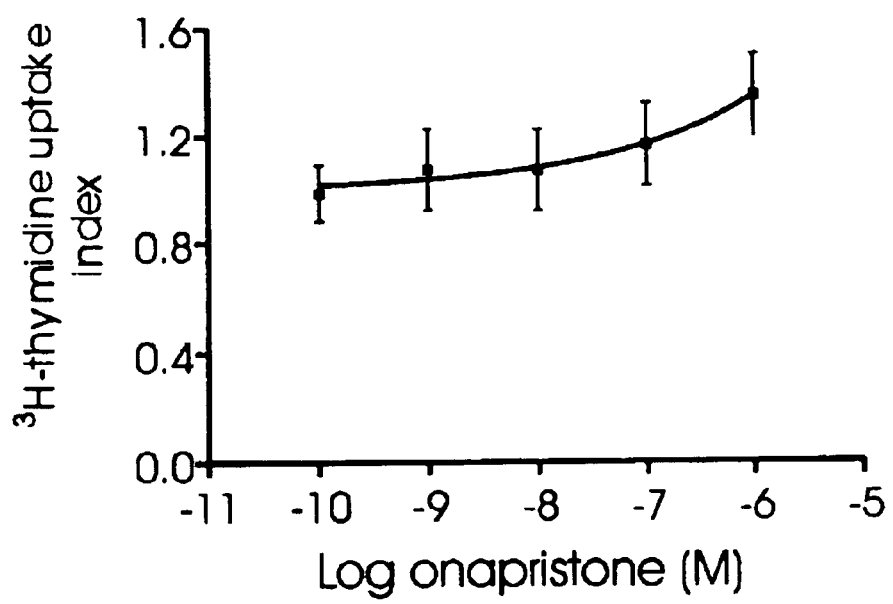
FIG. 4 illustrates the effect of ZK on MC4-L1 cell line proliferation. 3H-Thymidine uptake index represents the ratio between cpm of experimental group vs control. The mean value of 3–15 experiments is shown.

In early passages, a stimulatory effect of MPA, RU and $E_2$ was observed for MC4-L1. In later passages, the stimulatory effect of MPA was only evident ($p<0.05$) with uM concentrations of MPA (FIG. 1). In early passages (before passage number 16), $E_2$ stimulated cell proliferation while in later passages no significant effects were detected (FIG. 2). RU had an agonist effect in early passages and in latter passages the effects were similar to that of MPA (FIG. 3). ZK also stimulated cell proliferation at $\mu$M concentrations (FIG. 4).

Figure 5:
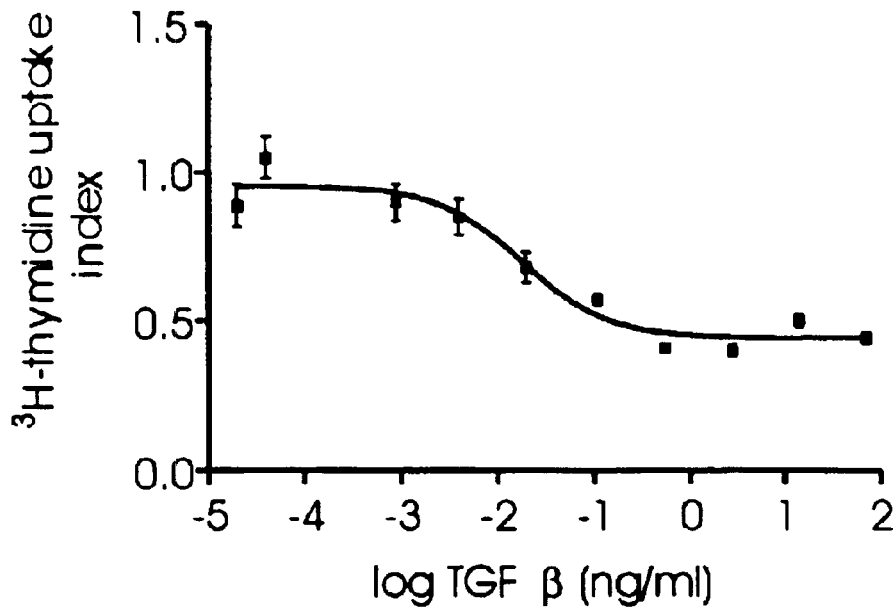
FIG. 5 illustrates the effect of TGFβ1 (ng/ml) on MC4-L1 cell line proliferation. 3H-Thymidine uptake index represents the ratio between cpm of experimental group vs control. The mean value of 3 experiments is shown.
Figure 6:
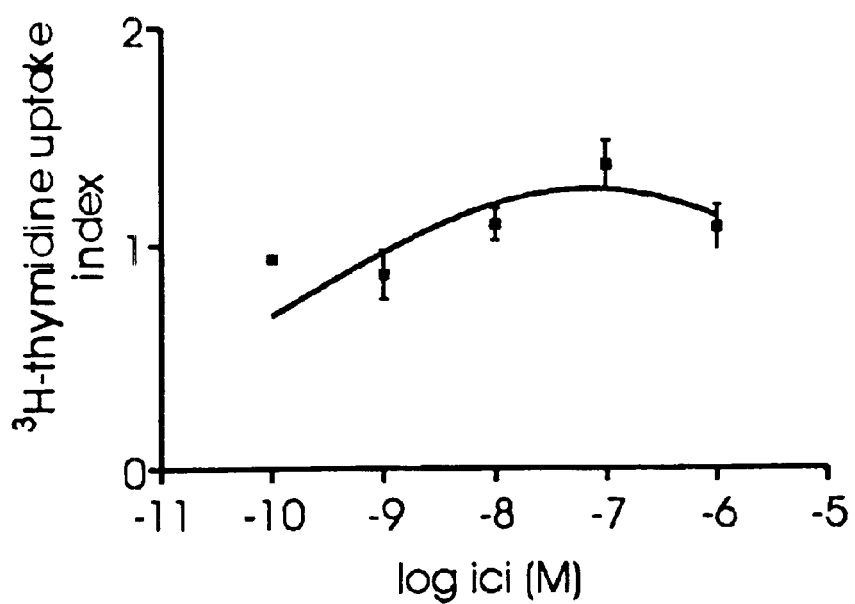
FIG. 6 illustrates the effect of ICI on MC4-L1 cell line proliferation. $^3$H-Thymidine uptake index represents the ratio between cpm of experimental group vs control. The mean value of 3 experiments is shown.

ICI and TGFβ1 were only assayed using later passages. TGFβ1 showed a significant inhibition of cell growth (FIG. 5) while ICI had no effect or occasionally exerted a proliferative effect (FIG. 6).

MC4-L2

Figure 7:
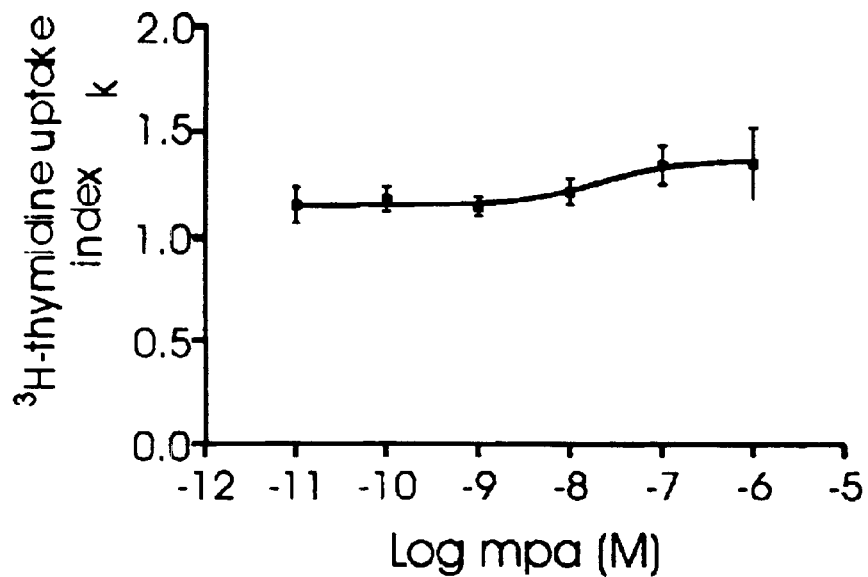
FIG. 7 illustrates the effect of MPA on MC4-L2 cell line proliferation. $^3$H-Thymidine uptake index represents the ratio between cpm of experimental group vs control. The mean value of 3–15 experiments is shown.
Figure 8:
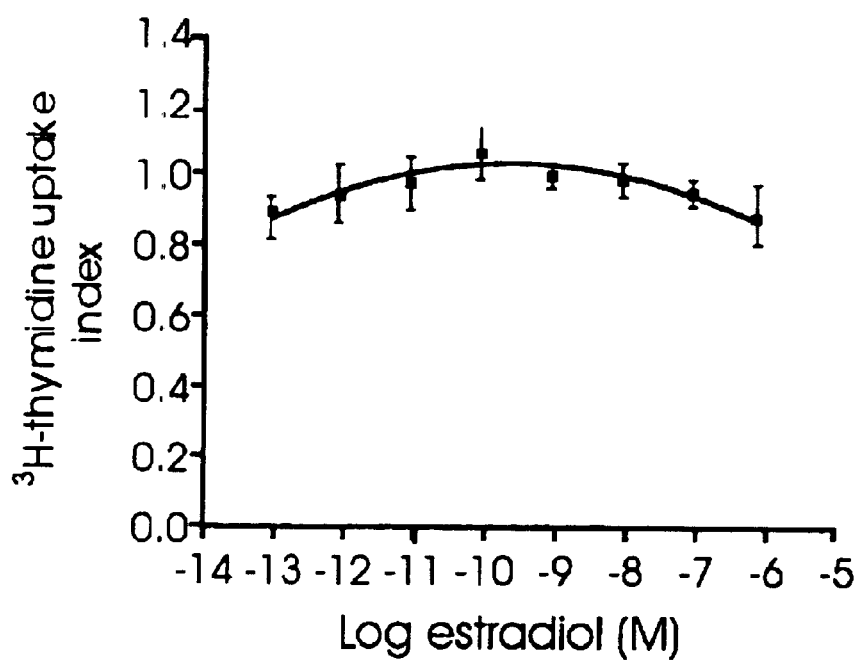
FIG. 8 illustrates the effect of estradiol ($E_2$) on MC4-L2 cell line proliferation. $^3$H-Thymidine uptake index represents the ratio between cpm of experimental group vs control. The mean value of 3–15 experiments is shown.

In this line a significant stimulatory effect was observed with MPA concentration ranging from 0.1 nM to about 10 nM (FIG. 7). $E_2$ stimulated cell proliferation at concentrations ranging from about 0.1 nM to about 10 nM (FIG. 8).

Figure 9:
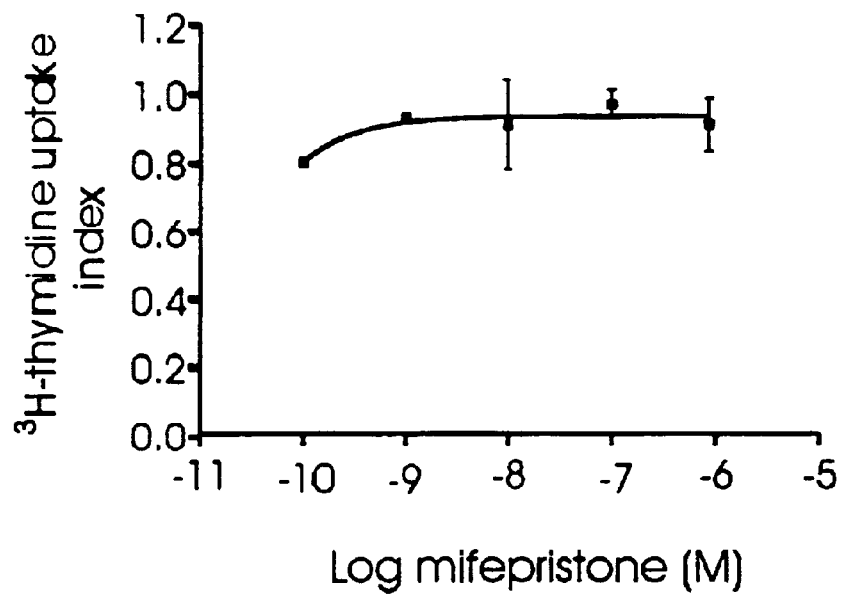
FIG. 9 illustrates the effect of RU on MC4-L2 cell line proliferation. $^3$H-Thymidine uptake index represents the ratio between cpm of experimental group vs control. The mean value of 3–15 experiments is shown.
Figure 10:
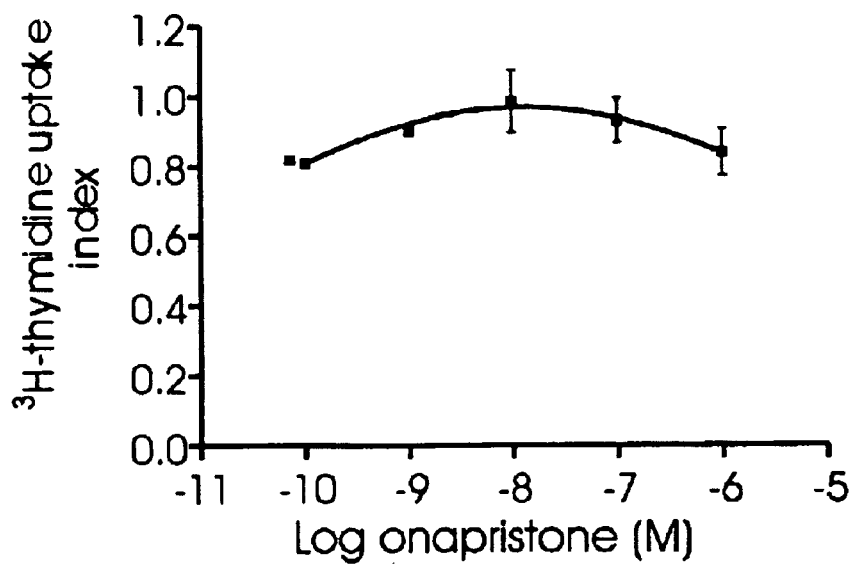
FIG. 10 illustrates the effect of ZK on MC4-L2 cell line proliferation. $^3$H-Thymidine uptake index represents the ratio between cpm of experimental group vs control. The mean value of 3–15 experiments is shown.
Figure 11:
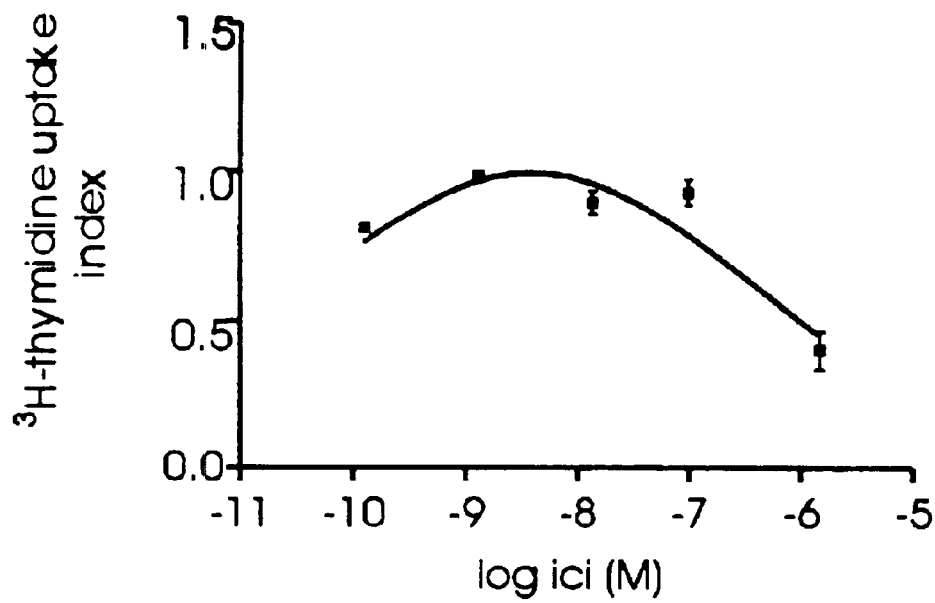
FIG. 11 illustrates the effect of ICI on MC4-L2 cell line proliferation. $^3$H-Thymidine uptake index represents the ratio between cpm of experimental group vs control. The mean value of 3 experiments is shown.
Figure 12:
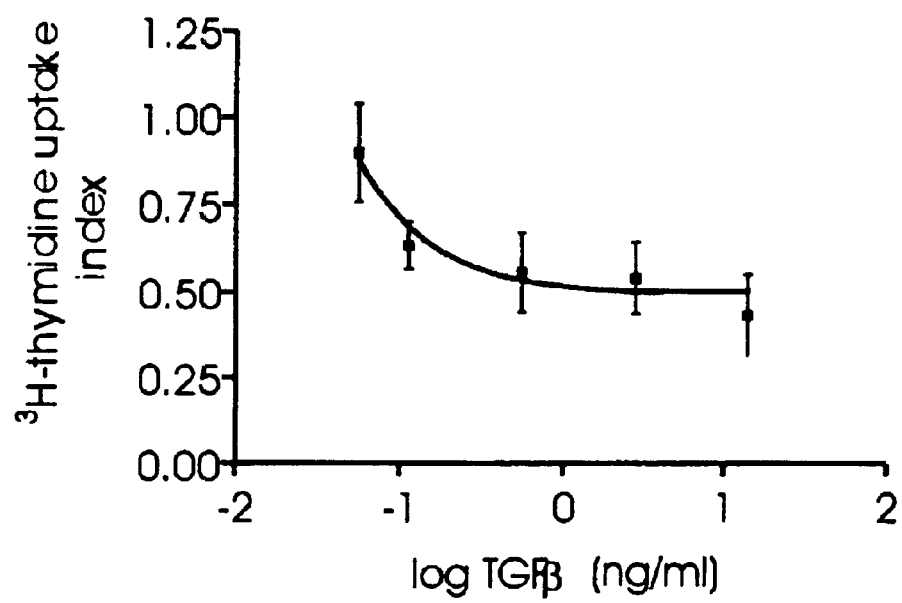
FIG. 12 illustrates the effect of TGFβ1 on MC4-L2 cell line proliferation. $^3$H-Thymidine uptake index represents the ratio between cpm of experimental group vs control. The mean value of 3 experiments is shown.

RU did not induce any change (FIG. 9) and ZK in some experiments showed an inhibitory effect when used in concentrations from about 0.1 to about 1 uM (FIG. 10). ICI was inhibitory at uM concentrations (FIG. 11) and TGFβ1 showed a similar inhibitory effect as that observed using MC4-L1 cell line (FIG. 12).

MC4-L3

No regulatory effects of hormones or anti-hormones were observed in the experimental conditions in which the other cell lines showed the reported effects.

MC7-L1

Figure 13:
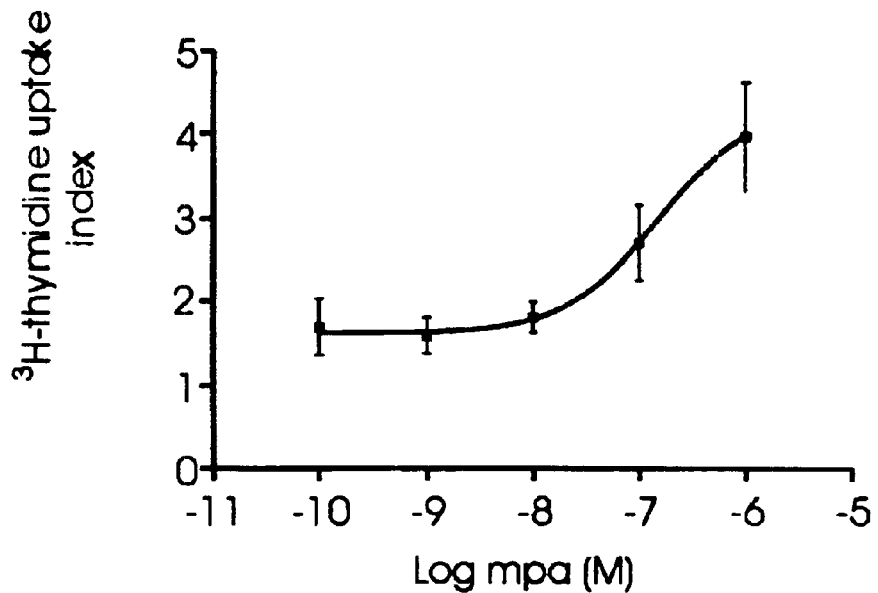
FIG. 13 illustrates the effect of MPA on MC7-L1 cell line proliferation. $^3$H-Thymidine uptake index represents the ratio between cpm of experimental group vs control. The mean value of 3–15 experiments is shown.
Figure 14:
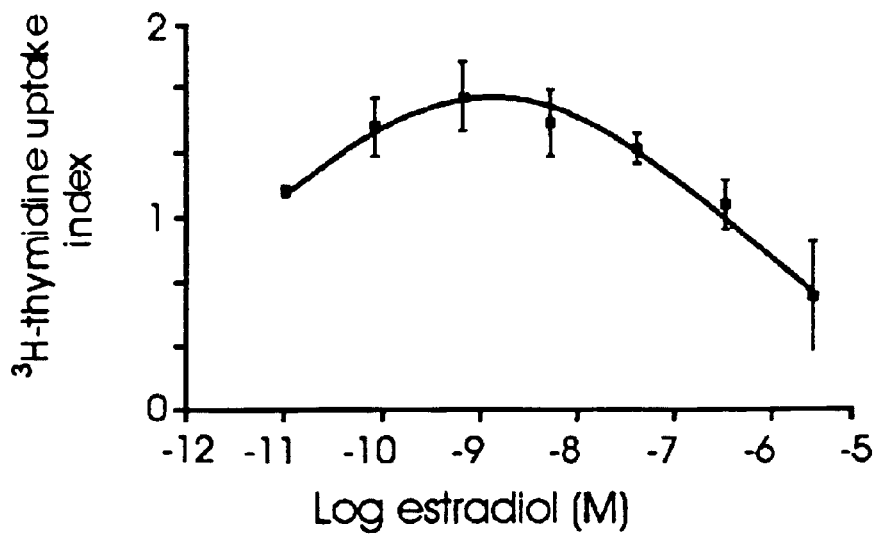
FIG. 14 illustrates the effect of estradiol ($E_2$) on MC7-L1 cell line proliferation. $^3$H-Thymidine uptake index represents the ratio between cpm of experimental group vs control. The mean value of 3–15 experiments is shown.
Figure 15:
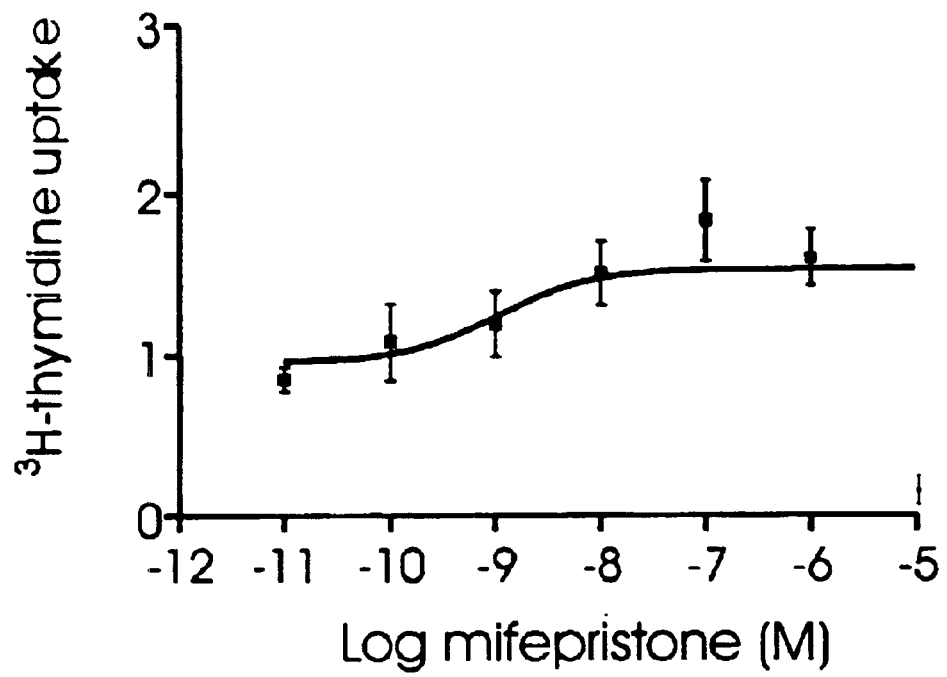
FIG. 15 illustrates the effect of RU on MC7-L1 cell line proliferation. $^3$H-Thymidine uptake index represents the ratio between cpm of experimental group vs control. The mean value of 3–15 experiments is shown.
Figure 16:
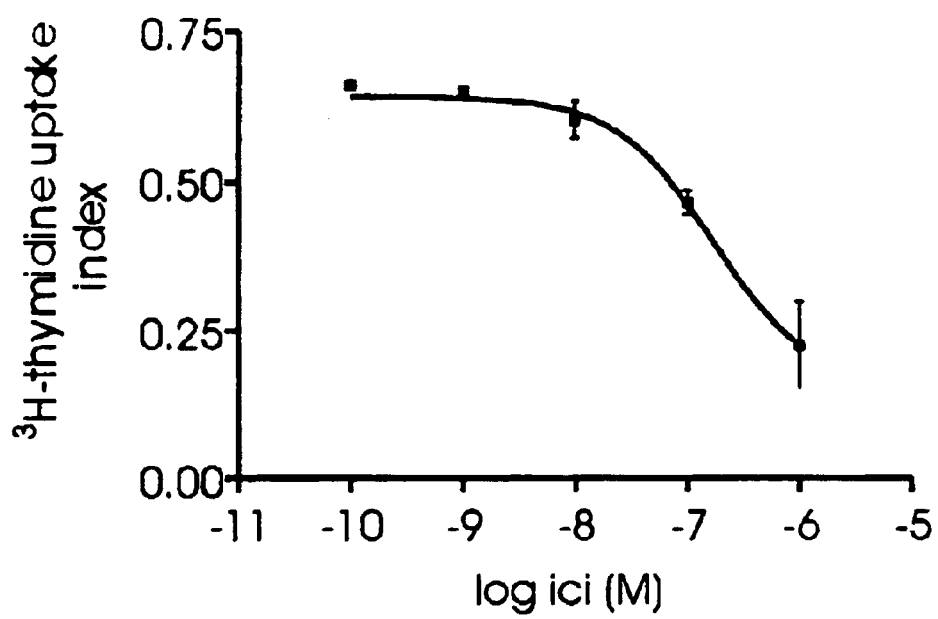
FIG. 16 illustrates the effect of ICI on MC7-L1 cell line proliferation. $^3$H-Thymidine uptake index represents the ratio between cpm of experimental group vs control. The mean value of 3 experiments is shown.

This was the most interesting line regarding in vitro hormone response. MPA significantly stimulates cell growth using about 1 nM to about 1 uM concentrations (FIG. 13). $E_2$ also stimulated cell proliferation at 100 nM to 1 μM but the higher values were preferently obtained about 1 nM concentrations (FIG. 14). RU also exerted a stimulatory effect, which was significant at about 0.1 to about 1 μM concentrations (FIG. 15). On the other hand, ZK did not modify thymidine uptake. ICI exerted an inhibitory effect at about 0.1 to about 1 μM concentrations (FIG. 16) and TGFβ1 had no effects.

In summary, the spindle shaped cell lines MC4-L2 and MC7-L1 were those which showed the major proliferative response to both MPA and $E_2$, and inhibitory response to ICI, being the later more sensitive. On the other hand, MC4-L2 was TGFβ1-responsive while MC7-L1 is unresponsive. This was the most significative difference found between both lines. Polygonal shaped cell lines were less responsive to all hormones and anti-hormones in the same experimental conditions although both cell lines (MC4-L1 and MC4-L3) were inhibited with TGFβ1.

For the purpose of the present invention, proliferation of cell lines were detected and measured by the uptake of modified nucleotides, such as and not limited to $^3$H-thymidine, $^{125}$IUDR (iododeoxyuridine); and dyes such as 3-(4,5-dimethylthiazol-2-yl)-2,5phenyltetrazolium bromide (MTT), which stains live cells.

In Vivo Hormone Response

MPA dependence

Figure 17:
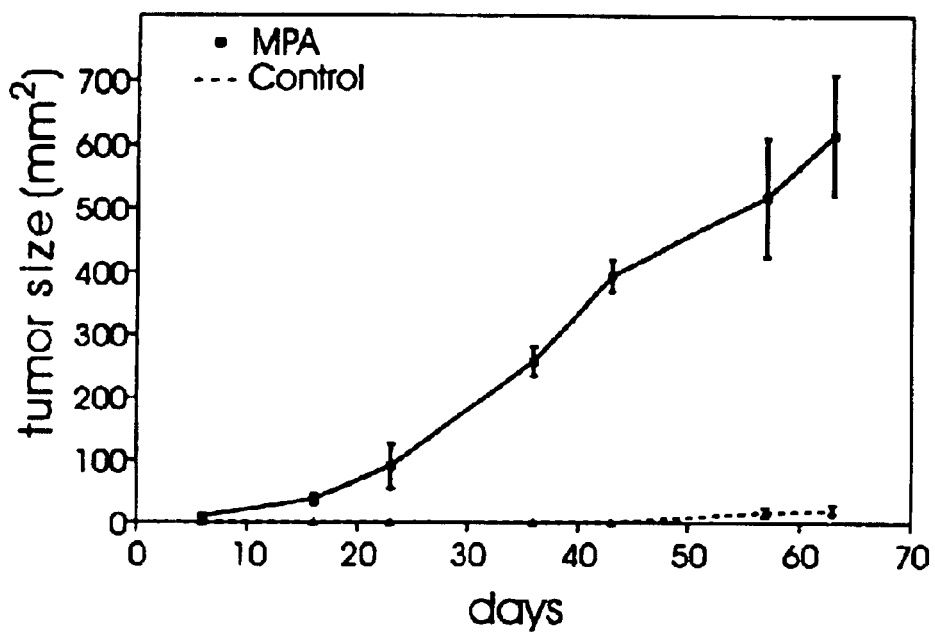
FIG. 17 illustrates the tumor size (mm2) of MC4-L1 cell line inoculated sc in BALB/c females mice treated or not with 40 mg MPA depot sc contralateral to tumor inoculum.

MC4-L1 was inoculated in MPA-treated and non-treated animals. As shown in FIG. 17, the same pattern of growth that was observed in the parental tumor line was observed here. When a later subculture (subculture 70) was inoculated, tumors grew with a similar pattern in treated and non-treated animals, although in the next passage growth was favored in UFA-treated animals, and in the 3rd passage, tumors were again MPA-dependent. A PI pattern of growth was observed with lines MC4-L2 and MC7-L1, while a PD pattern characterized line MC4-L3.

Estrogen and antiprogestin response

Figure 18:
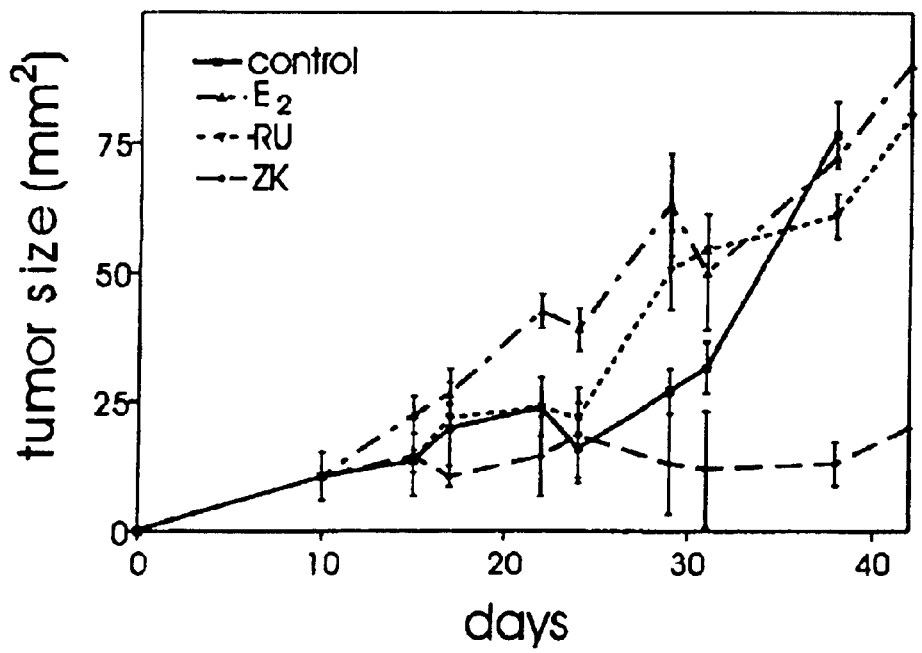
FIG. 18 illustrates the effect of RU, $E_2$ and ZK on tumor size (mm2). Mice bearing MC4-L1 tumors of about 50 mm2 were treated daily with ZK (10 mg/Kg weight) or RU (6.4 mg/Kg weight) or implanted with 5 mg $E_2$ silastic pellets.

Animals bearing MC4-L1 tumors, growing very slowly due to the absence of MPA, were treated with $E_2$, RU and ZK as mentioned in example 8. Only animals treated with ZK showed tumor regression (FIG. 18).

Figure 19:
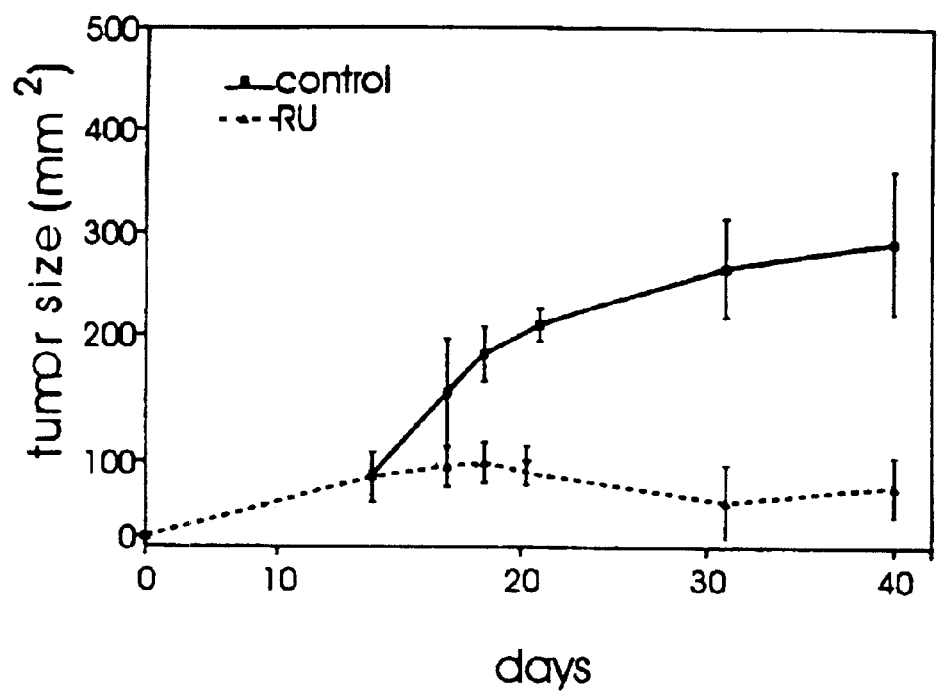
FIG. 19 illustrates the effect of RU on tumor size (mm2). Mice bearing MC4-L2 tumors of about 50 mm2 were treated daily with RU (6.4 mg/Kg weight).
Figure 20:
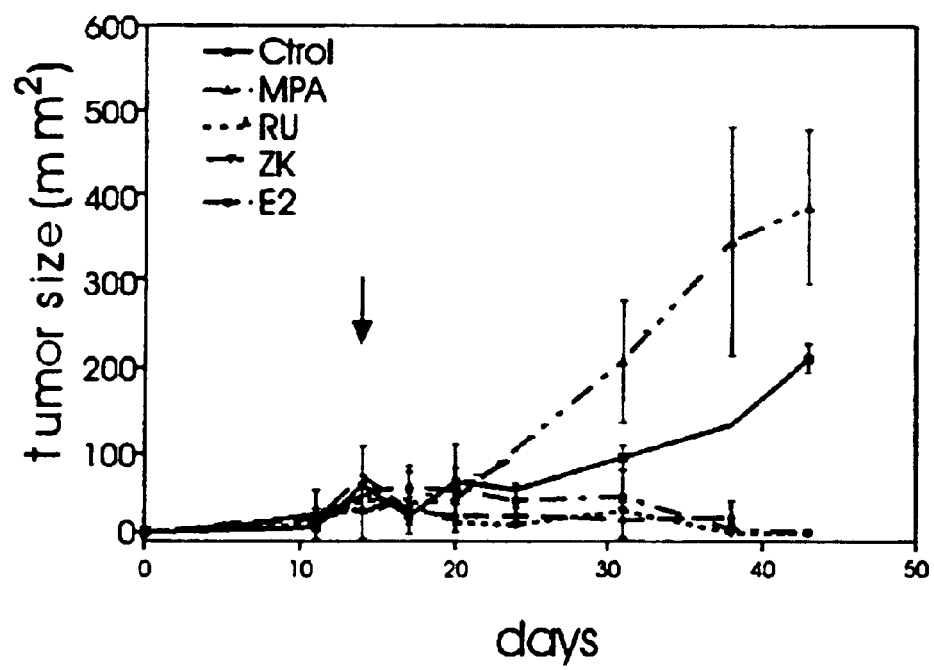
FIG. 20 illustrates the effect of RU, $E_2$ and ZK on tumor size (mm2). Mice bearing MC4-L3 tumors of about 50 mm2 were treated daily with ZK (10 mg/Kg weight) or RU (6.4 mg/Kg weight) or implanted with 5 mg $E_2$ silastic pellets.

In MC4-L2, complete regression was observed in animals treated with RU (FIG. 19). Complete regression was observed in MC4-L3 tumor line using any of the three agents RU, ZK or $E_2$. As illustrated in FIG. 20, the MC7-L1 tumor line was not inhibited neither by RU, ZK, nor $E_2$.

In summary, spindle shaped cells (MC4-L2 and MC7-L1 ), when transplanted in syngeneic mice, gave rise to PI tumors, while polygonal cell lines (MC4-L1 and MC4-L3) gave rise to PD tumors. Spindle-shaped cells responded differently to hormone treatment: while MC4-L2 was inhibited by RU, MC7-L1 was resistant to all treatments. In addition, polygonal cells showed a different pattern of response: while MC4-$L_1$ regressed only with ZK treatment, MC4-L3 cells regressed with ZK, RU and $E_2$.

One skilled in the art also is aware of means to monitor a therapeutic response upon administering hormone or related molecules. In particular, the therapeutic response can be assessed by monitoring partial or complete tumor regression and/or number of metastases and/or survival. The attenuation of tumor growth or tumor regression in response to treatment can be monitored using several end points known to those skilled in the art including, for example, tumor mass or size, reduction/prevention of metastasis or prolongation of survival. These described methods are by no means all-inclusive, and further methods to suit the specific application will be apparent to the ordinary skilled artisan.

Karyotype

The modal number of each line is shown in Table 2. These were evaluated with passages 18–22 of each cell line. MC4-L2 shows two modal numbers. Similar cytogenetic markers were detected in all lines and they are being characterized.

TABLE 2

Main features of the cell lines developed

| Cell lines | MC4-L1 | MC4-L2 | MC4-L3 | MC7-L1 |
|---|---|---|---|---|
| Parental tumor | CC4-HD | CC4-HD | CC4-HD | C7-HI |
| In vitro morphology | polygonal | spindle shaped | polygonal | spindle shaped |
| Detachment | >10 min. | <1 min. | >10 min. | <7 min. |
| Duplication time (hs) | 24 | 19 | 25 | 20 |
| Modal number | 65 | 68–83 | 60 | 74 |
| RE (fmoles/mg prot) | 1.27 | 20.8–9.6 | 2.69 | 13.8 |
| RE (IMH) | +++ | +++ | +++ | +++ |
| RP (fmoles/mg prot) | 3.65–13.48 | 164–145 | 6 | 141 |
| RP (IMH) | +++ | ++ | +++ | ++ |
| Cytokeratin in vitro | +++ | ++ | ++ | ++ |
| c-erbB2 in vitro (IMH) | ++++ | ++++ | ++++ | + |
| In vitro MPA proliferative response | ± | ++ | − | ++++ |
| In vitro $E_2$ proliferative response | ± | + | − | ++ |
| In vitro antiestrogen response | No inhibition or slightly proliferative | Inhibitory | No | Inhibitory |
| Inhibitory response to TGF 1 | +++ | +++ | +++ | − |
| In vivo progestin-dependence | PD | PI | PD | PI |
| RE and RP in tumor sections (IMH) | +++ | +++ | +++ | +++ |
| Cytokeratins in tumor sections | positive | positive | positive | positive |
| Tumor morphology | Ductal infiltrating carcinoma | Fuso-cellular carcinoma | Ductal infiltrating carcinoma | Undifferentiated carcinoma |
| Local invasion | poor | high | poor | very high |
| Metastasis | lung | Axilar and lung | lung | Axilar, lung and others |

The inventors have developed four different mouse mammary cell lines originated in two different in vivo tumor lines that express ER and PR. These are the first mouse mammary adenocarcinoma cell lines that express ER and PR and are hormone responsive, excluding the lines originated in transgenic mice (Sacco MG. Et al 1998 Breast Cancer Res and Treat 47:171–180).

Three out of four lines derived from the same in vivo tumor line and two out of three from the same primary culture. These lines have been described independently because they have different properties regarding morphology, hormone dependence and karyotypic analysis. Two lines have polygonal morphology (MC4-L1 and MC4-L3) and the other two are spindle shaped cells (MC4-L2 and MC7-L1 ). A different pattern of invasion and metastasis was observed associated to these types of morphology. This may render the lines useful to evaluate the relation between hormone sensitivity, invasion and metastases.

The polygonal shaped lines showed an MPA-responsive growth pattern when inoculated in syngeneic mice, while the spindle shaped cells grew similarly in treated or untreated mice. The opposite effect was observed in in vitro studies. The spindle-shaped cells were stimulated both with MPA and with E2; in the polygonal cells the stimulatory effect was found only in early passages.

Treatment with antiprogestins in vitro yield unexpected results: RU acted as an agonist at high concentrations (from about 100 nM to about 1 $\mu$M), in experiments where MPA was proliferative while ZK had no effects or was slightly inhibitory are high concentrations (1 $\mu$M). The antiestrogen ICI was inhibitory in the spindle shaped cell lines at uM concentrations.

In vivo treatment with antiprogestins gave responses different to that obtained in in vitro studies: a difference between MC7-L1 and MC4-L2 was evident: while MC7-L1 was unresponsive to RU, ZK and E2. MCL2 was inhibited by RU. MC4-L1 tumors regressed only with ZK while in MC4-L3 RU, ZK and E2 induced tumor regression. TGF$\beta$1 induced inhibition in all cell lines except in MC7-L1.

All these data regarding hormone responsiveness indicate that this panel of cell lines are particularly interesting to study hormone action and thus to evaluate the role of new pharmacological compounds, or to test the presence of xeno-estrogens and other environmental agents. All lines share the same property: their similar origin and the presence of both estrogen and progesterone receptors. In spite of this, each one has individual characteristics that may render them appropriate for different research lines.

The action of steroid hormones has been oversimplified for years. In the last years, different non-classical effects of hormones are being considered and these effects include for example actions at membrane level. The fact that in vitro studies antiprogestins may act as agonists instead of being antagonists, and that the opposite effects are obtained when administered in vivo, makes of this panel of cell lines an excellent tool to study the in vivo effects of hormones vs in vitro effects. This is one of the best advantage of this panel of cell lines. In vivo experiments can very easily be carried out. Usually, human cell lines must be inoculated in immunodeficient animals to avoid rejection. This is the best approximation to the clinical situation although there are obvious differences between this experimental situation and the inoculation the cells of the present invention into syngeneic mice.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Primary Cultures

Tumors were aseptically removed, minced and washed with DMEM/F12 (Dulbecco's modified Eagle's medium: Ham's F12, 1:1, without phenol red, 100 U/ml penicillin and 100 $\mu$g/ml streptomycin). The tissue was suspended in 5 ml of enzymatic solution (trypsin: 2.5 mg/mi, albumin: 5 mg/ml and collagenase type II 850 U/ml in phosphate buffered saline (PBS) and incubated at 37° C. for 20 min., under continuous stirring. The liquid phase of the suspension was then removed and the undigested tissue incubated for an additional 20 min., with fresh enzymatic solution. Enzyme action was stopped by adding washing medium (WM) (DMEM/F12+5% FCS (Gen S. A. Buenos Aires). Epithelial and fibroblastic cells were separated by a modification of the sedimentation technique described previously (Dran et al., 1995). Briefly, the cell suspension obtained was resuspended in 15 ml of fibroblastic medium (FM) (DMEM/F12+10% heat inactivated FCS) and allowed to sediment for 20 min. The upper 5 ml, corresponding to the fibroblastic fraction, was seeded in flasks, and the cells were allowed to attach during 1–2 hours after which the medium containing unattached cells was removed and replaced by fresh FM. The sedimented cells correspond to the epithelial enriched fraction, which was resuspended again in 15 ml of WM and allowed to sediment for other 20 min. The upper 15 ml were discarded and this procedure was repeated 10 times more or less until no fibroblast were detected in the supernatant. Cells were plated in culture flasks with epithelial medium (EM) (DMEM/F12+5% chFCS) and allowed to attach for 24–48 hrs. The medium was then removed and replaced by fresh medium containing 10–8 M MFA. The medium was changed every 2–3 days. At confluence, or when cell clusters looked overcrowded, the cells were detached with 0.25% trypsin, washed, and resuspended in fresh EM. The resulting suspension was used in the different assays.

Example 2

Establishment of Cell Lines and Culture Conditions

Tissue used to establish the cell lines was obtained from MA-induced tumor, a PD carcinoma (CC4-HD) at passage 60, maintained by syngeneic transplantation in MPA-treated mice, and a PI tumor (C7-HI) was maintained by syngeneic transplantation in untreated female mice.

Epithelial enriched cultures growing in the presence of DMEM/F12 (Sigma Chemical Co, St Louis Mo.) and 5% chFCS (Gen S.A. Buenos Aires) and 10 nM MPA (Sigma Chemical Co, St. Louis Mo.) were now grown in the same medium with the addition of 10% FCS (Life Technologies, Inc., Grand Island, N.Y.), glutamine 2 mM (Life Technologies), bovine insulin (2 $\mu$g/ml) (Life Technologies, Inc., Grand Island, N.Y.), penicillin 100 U/ml streptomycin 100 $\mu$g/ml, Amphotericin B (Life Technologies, Inc., Grand Island, N.Y.), Tiroxin (10 nM) (Sigma Chemical Co, St. Louis Mo.), cortisol (0.3 $\mu$M) (Sigma Chemical Co, St. Louis Mo.), transferrin (10 ng/ml) (Sigma Chemical Co, St. Louis Mo.) and 10 nM MPA (Sigma Chemical Co, St. Louis Mo.). Ten days after seeding, cells became vacuolated and some of them started to detach; fibroblasts, which were very scanty at the beginning, increased in proportion.

Some wells were subcultured from big wells to smaller ones. That means from one well from a 6 well plate to one well of a 24 well plate. The cells which did not attach for the first hour were then transferred to another well, and the cells which did not attach in this second well for two hours were then transferred to another well. This was performed in order to remove fibroblasts. Curiously, cell lines arose from epithelial clusters present in these fast attaching cell-populations. Five or six subcultures were performed during 3–4 months, and in each subculture less cells were harvested. From 2 different primary cultures performed of the CC4HD tumor lines, 3 cell lines were developed, one of them, MC4-L2, is a subline derived from MC4L1. A small group of cells from passage 7 of MC4-L1 remained attached after trypsinization, and with time these cells started to grow with completely different pattern than that of the parental cells.

A similar phenomenon was observed with MC7-L1. Colonies of giant cells could also be seen but in this case there were different kind of cells, intermingled with giant fibroblastic-like cells and the cell line arose from wells where the general morphological aspect was of scanty epithelial cells intermingled with a mass of fibroblast-like cells.

Example 3

Doubling Time Assay

Doubling time of the cell lines was determined by plating the cells in 6 well plates at 20,000 cells/well and counting duplicate wells at 9 am and 5 pm for one week. Doubling times were calculated from the log phase of the growth curves.

Example 4

Immunohistochemistry Assay

Cell lines were grown on eight-well chamber slides. Slides were prepared for staining by rinsing three times in PBS, fixing for 45 min in buffered formalin 15% and drying until used. Tumor tissue was fixed in buffered formalin for ER, PR and c-erbB2, or ethanol for cytokeratins at 1:1000 dilution and paraffin-embedded by standard methods. 4 $\mu$m sections were cut and stained with H&E by standard methods. Immunostaining for cytokeratin was performed using rabbit polyclonal antibody ZO622 (Dako Corp., Carpinteria, Calif.). ER (1:50 in tissues and 1:100 chamber slide) and PR (1:100 in tissue and 1:200 chamber slide) rabbit polyclonal antibodies were obtained from Santa Cruz Biotechnology Inc, Santa Cruz, Calif., and PR monoclonal antibody (1:250 in chamber slides) was obtained from Neomarkers. Staining was visualized using Vectastin Elite ABC immunoperoxidase system (Vector Laboratories, Burlingame, Calif.) and 3,3'-diaminobenzidine peroxidase substrate kit (Vector Laboratories, Burlingame, Calif.). Cells were counterstained with a weak hematoxylin stain. Primary antibody was replaced with normal serum rabbit for negative controls.

Example 5

Tumorigenicity Cell Line Assay

Cells were trypsinized and resuspended in 10 fold excess of culture medium and 10% FCS. After centrifugation cells were resuspended in serum-free medium and 106 cells were injected sc in a final volume of 0.1 ml using a 21 gauge needle in the right inguinal flank of BALB/c mice which have been inoculated contralaterally with 40 mg MPA depot (Gador Laboratories, Buenos Aires). The mice were examined every three days for the development of palpable tumors. At the end of the experiment the animals were killed and the tumors excised. Complete autopsies were performed to detect the presence of metastases. Animal care was in agreement with institutional guidelines.

Example 6

Karyotypic Analysis

Semi confluent cells were exposed to 1 $\mu$g/ml colcemid for 2 hs at 37° C., and then detached with trypsin. Hypotonic treatment was performed in 0.075M potassium chloride for 10 min an the cells were fixed with 3:1 methanol—glacial acetic acid. The slides were stained with 3% Giemsa for morphological examination and chromosome counting. G-banding was performed by heating at 60° C. overnight and staining with Wright stain freshly diluted 1:3 in Phosphate buffer, pH 6.8.

Example 7

Assay for the Presence of ER and PR

The presence of ER and PR was evaluated by immunocytochemistry as described above, and by ligand binding using the whole cell technique at single saturation points (Dran et al., 1995 supra).

Example 8

Evaluation of Hormone Dependence

In vitro assay

The response of different cell lines to MPA, E2, RU, ZK or TGF$\beta$1 were evaluated.

3H-Thymidine uptake: In a 96 well microplate, 0.1 ml/well of a cell suspension were seeded in EM at a concentration of $10^5$ cell/ml. After attachment (24 hs), the cells were incubated for 72 hs with the experimental solutions to be tested. Half the media was changed every 24 hs. The cells were incubated with 0.4 $\mu$Ci of $^3$H-thymidine (specific activity: 20 Ci/mmol) for 24 hs, trypsinized and harvested in a cell harvester. Filters were counted in a liquid scintillation counter. Assays were performed in octuplicates and mean and standard deviation were calculated for each solution tested. The difference between controls and experimental groups were analyzed by ANOVA followed by Dunnet's t test between groups.

In vivo assays

Cells from different lines were inoculated into BALB/c female mice treated or not with MPA as described previously. If tumors grew similarly in treated and untreated animals, the tumors growing in untreated mice were used for the next passage. Tumors were transplanted by trocar sc in the right inguinal flank of 2 month old, BALB/c female mice. Hormone treatments were initiated when the tumors reached around 50 mm2. RU (6.5 mg/Kg body weight) and ZK (10 mg/Kg body weight) were inoculated as daily sc injections. $E_2$ was administered as 5 mg silastic pellets implanted sc. Tumor growth was measured every 2–3 days.

Various modifications of the invention in addition to those shown and described herein will be apparent to those skilled in the art from the foregoing description. Such modifications are also intended to fall within the scope of the appended claims

What is claimed is:

1. A non transgenic mouse mammary adenocarcinoma cell line, wherein the cell line is selected from the group consisting of MC4-L1 (ATCC# PTA-889), MC4-L3 (ATCC# PTA-891), MC4-L2 (ATCC# PTA-892) and MC7-L1 (ATCC # PTA-890).

2. A kit for evaluating the proliferation of cells, wherein the kit comprises an aliquot of a cell line selected from the group consisting of MC4-L1 (ATCC# PTA-889), MC4-L3 (ATCC# PTA-891), MC4-L2 (ATCC# PTA-892) and MC7-L1 (ATCC # PTA-890).

* * * * *